(12) United States Patent
Kaminski

(10) Patent No.: US 8,567,266 B2
(45) Date of Patent: Oct. 29, 2013

(54) METHOD AND DEVICE FOR MEASURING DUST CONCENTRATION IN FLOWING GAS

(76) Inventor: Stanislaw Kaminski, Warszawa (PL)

( * ) Notice: Subject to any disclaimer, the term of this patent is extended or adjusted under 35 U.S.C. 154(b) by 286 days.

(21) Appl. No.: 13/124,863

(22) PCT Filed: Nov. 6, 2008

(86) PCT No.: PCT/PL2008/000080
§ 371 (c)(1),
(2), (4) Date: Apr. 19, 2011

(87) PCT Pub. No.: WO2010/053386
PCT Pub. Date: May 14, 2010

(65) Prior Publication Data
US 2011/0203350 A1    Aug. 25, 2011

(51) Int. Cl.
*G01N 1/22*    (2006.01)
(52) U.S. Cl.
USPC .................... 73/863.51; 73/863.41; 73/863.56
(58) Field of Classification Search
USPC .............. 73/863.21, 863.22, 863.41, 863.51, 73/863.52, 863.83, 864.81
See application file for complete search history.

(56) References Cited

U.S. PATENT DOCUMENTS

| | | | |
|---|---|---|---|
| 2,982,131 A | | 5/1961 | Rosinski |
| 3,261,199 A | * | 7/1966 | Raynor ....................... 73/863.03 |
| 3,587,323 A | * | 6/1971 | Benjaminson ............. 73/863.21 |
| 3,672,225 A | * | 6/1972 | Louis ......................... 73/863.58 |
| 3,681,973 A | * | 8/1972 | Ludwig ........................ 73/28.06 |
| 3,914,979 A | * | 10/1975 | Shofner ......................... 73/28.05 |
| 3,954,428 A | * | 5/1976 | Marple et al. .................... 96/417 |
| 4,091,835 A | * | 5/1978 | Frampton ................... 73/863.51 |
| 4,141,238 A | | 2/1979 | Steen |
| 4,159,635 A | * | 7/1979 | Sehmel ....................... 73/863.22 |
| 4,221,130 A | * | 9/1980 | Burrows ..................... 73/863.58 |
| 4,475,379 A | * | 10/1984 | Jinotti ........................... 73/28.01 |
| 4,566,342 A | * | 1/1986 | Kurz ........................... 73/863.03 |
| 4,876,902 A | * | 10/1989 | von Alfthan et al. ...... 73/863.83 |
| 4,942,774 A | * | 7/1990 | McFarland ................. 73/864.81 |
| 5,090,257 A | * | 2/1992 | Bruce ......................... 73/863.03 |
| 5,443,271 A | * | 8/1995 | Holsen et al. .............. 73/863.22 |
| 6,553,848 B1 | * | 4/2003 | Tallentire et al. .......... 73/864.81 |
| 6,584,865 B1 | | 7/2003 | Doherty et al. |
| 6,777,228 B2 | * | 8/2004 | Lejeune ....................... 435/309.1 |
| 7,571,657 B2 | * | 8/2009 | Ramsey ..................... 73/863.21 |
| 8,171,807 B2 | * | 5/2012 | Carichon et al. ........... 73/863.51 |
| 8,210,056 B2 | * | 7/2012 | Pike et al. ........................ 73/863 |
| 2004/0237672 A1 | * | 12/2004 | Jaeger ........................ 73/863.31 |

FOREIGN PATENT DOCUMENTS

| | | |
|---|---|---|
| EP | 1413873 | 4/2004 |
| GB | 1442538 A | 7/1976 |

* cited by examiner

*Primary Examiner* — David A Rogers
(74) *Attorney, Agent, or Firm* — Christopher L. Parmelee; Walker & Jocke

(57) ABSTRACT

A method and device is provided for measuring dust in a flowing gas, particularly atmospheric air. The device includes an intake nozzle which is configured such that aerodynamic forces continuously position the intake nozzle along the direction of gas flow. The velocity of the measuring stream in the inlet of the intake nozzle is compared with the velocity of gas flowing around the intake nozzle. The possible difference between the measured velocities is compensated by changing the velocity of the measuring stream in a mechanical way such as with a suction pump.

14 Claims, 5 Drawing Sheets

METHOD AND DEVICE FOR MEASURING DUST CONCENTRATION IN FLOWING GAS

FIELD OF THE INVENTION

Figure 1:
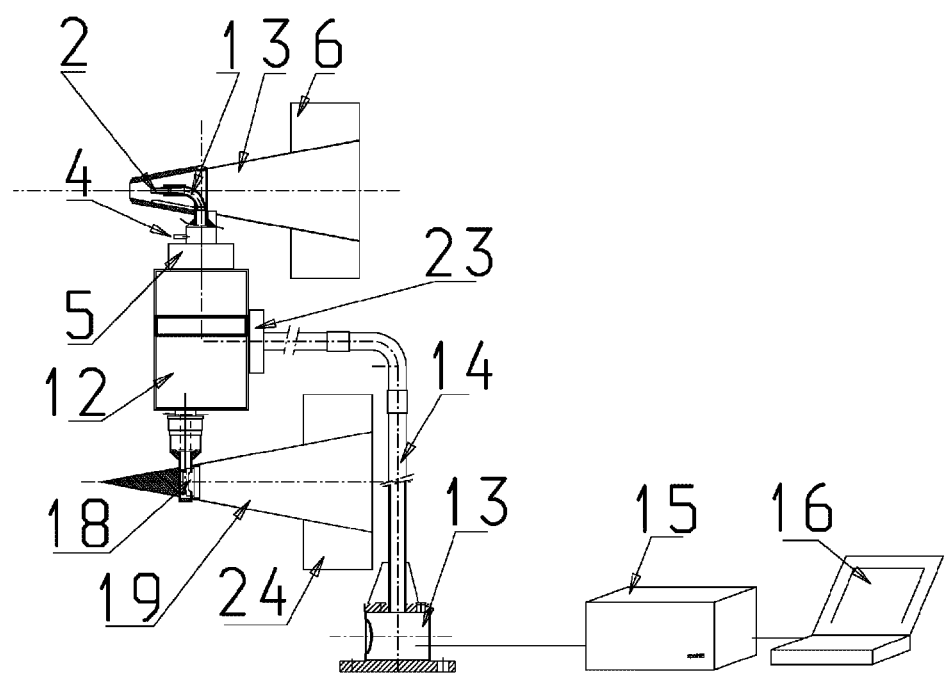

The present invention relates to the method of measuring dust concentration in flowing gas, particularly atmospheric air, and the device for measuring the same.

BACKGROUND OF THE INVENTION

A method is known for measuring dust concentration in a stream of flowing gas, which consists in taking the measuring gas stream by using an intake nozzle along the direction of gas flow, then measuring the size of dust particles and/or separating the dust and measuring its mass.

A device is also known for measuring dust concentration in a stream of flowing gas, particularly atmospheric air, which features a module for taking a sample of flowing gas and a dust sampler, wherein the dust sampler possibly includes a dust sensor, and further possibly a dust filter, and still further possibly a dust separator, and the said dust sampler further includes an immovable body containing a unit for measuring the parameters of gas flow and a suction pump with a control circuit and, possibly, a unit for measuring the temperature and humidity of flowing gas.

Known solutions do not take into account the influence of variations in direction and velocity of flowing gas, particularly variations in wind speed occurring during measurement, on the accuracy of measurement. The above factors have a significant impact on concentration of dusty contaminants at the inlet of the intake nozzle. Therefore, known methods and devices for measuring dust concentration in flowing gas practically produce totally distorted measurement results.

The purpose of the present invention is to disclose the method and device for measuring the concentration of dust in a stream of flowing gas, particularly atmospheric air, which allows eliminating the influence of variations in direction and velocity of flowing gas on measurement results.

DISCLOSURE OF THE INVENTION

The present invention is directed to the method of measuring dust concentration in flowing gas, particularly atmospheric air, consisting in taking the measuring stream of gas by using an intake nozzle along the direction of gas flow, measuring the dust particle size and possibly separating dust, with the flow not being corrected by measuring the wind speed, wherein the intake nozzle is continuously positioned aerodynamically along the direction of flowing gas, the velocity of measuring stream flowing in the inlet of intake nozzle is compared with velocity of gas flowing around the intake nozzle, and possible differences between these velocities are compensated by mechanically changing the velocity of measuring stream.

Preferably, velocity of measuring stream in the inlet of the intake nozzle is determined based on the flow parameters of the said stream determined during the measurement of dust particle size. Also preferably, water drops present in the stream of gas sucked into the nozzle are evaporated by using laser light delivered to the measuring stream through an optical fiber located at a wider end of the Venturi tube and directed upwards along the axis of the said Venturi tube towards the smallest cross-sectional area of the Venturi tube.

Further, the present invention is directed to the device for measuring dust concentration in flowing gas, particularly atmospheric air; the said device consisting of a feeding pipe with an inlet nozzle or a circular slot, a dust sensor or a filter, possibly with a dust separator, and an immovable body that contains circuits for measuring gas flow, temperature and humidity, and a suction pump with a control circuit, wherein the feeding pipe is hermetically connected to the meter that measures the velocity of inner flowing gas and to the controlling element having the form of an open diffuser, whereas the intake nozzle is positioned inside the diffuser, whereas the inlet of intake nozzle is directed towards that end of diffuser which has smaller diameter, whereas the end of the feeding pipe located opposite to the intake nozzle is connected in a rotary manner to the unit for measuring, inner flow parameters, whereas the particle sensor, suction pump and exhaust pipe with an exhaust nozzle are also connected to this unit, the latter exhaust pipe is connected to this unit in a rotary manner and is joined stiffly with a conical fairing, while the exhaust nozzle is located inside the said conical fairing and the outlet of the said exhaust nozzle is directed towards the base of the said conical fairing.

Preferably, the said diffuser and fairing include at least one vertical stabiliser located near the end of greater diameter, and the diffuser at the end with a smaller diameter is shaped in the form of a Venturi tube employed as a meter for measuring the velocity of flowing gas, and the second part of the said meter has the form of a Pitot tube located above the lower fairing, and the intake nozzle and diffuser are arranged coaxially. Also preferably, the meter for measuring the velocity of flowing gas includes, as the first part, the Pitot tube located under the upper diffuser and, as the second part, the openings located above the lower fairing perpendicularly to the axis of the said lower fairing, and the said meter for measuring the velocity of flowing gas is a combination of a Pitot tube and a Venturi tube, and the Pitot tube has an additional shield in the form of a pipe with a greater diameter and equipped with the filter; alternatively the meter for measuring the velocity of flowing gas is built in the form of a Prandtl pipe.

Preferably, the unit for measuring the inner flow parameters includes a Venturi tube, possibly equipped with humidity and temperature sensors, and an optical fibre. Still preferably, the particle sensor is equipped with NIRS (Near Infrared Spectroscope). Also preferably, the filter seated in the socket is located between the particle sensor and suction pump. Further preferably, the unit for measuring inner flow parameters, the particle sensor, the suction pump and possibly the filter are all located inside the immovable body fixed to the base directly or possibly by using a rigid extension arm. It is preferred when there is a tight, lockable electrical connection between the immovable body and the extension arm. It is also preferred when the body is tightly covered with insulating foam and the temperature regulator is located inside the body. Still preferably, the feeding pipe is rigidly connected with an electric or magnetic wind-rose meter, and the magnetic sensor of wind-rose meter is located beyond the axis of rotation.

Further, the present invention is also directed to the device for measuring dust concentration in flowing gas, particularly atmospheric air; the said device consisting in the unit for taking a sample of gas and a dust sampler, and the said gas sample taking unit includes a feeding pipe with an intake nozzle, and a dust sampler possibly includes a dust sensor, and further possibly a dust filter, and still further possibly a dust separator, and the said dust sampler further includes an immovable body containing a unit for measuring the parameters of inner gas flow and a suction pump with a control circuit and, possibly, a unit for measuring the temperature and humidity of flowing gas, wherein the said feeding pipe is connected hermetically to the intermediate chamber and is also connected stiffly to the control unit which is shaped in the form of an open diffuser, whereas the intake nozzle is located inside the said diffuser and the inlet of the said intake nozzle is directed towards that end of the said diffuser which has a smaller diameter, while the end of the feeding pipe opposite to the said intake nozzle is connected in a rotary manner with the said intermediate chamber which is hermetically put on the head of the connected dust sampler.

Both the method and device according to the present invention ensure that during the entire measurement period the isokinetic condition is met, i.e. air velocity inside the inlet of the intake nozzle is equal to the velocity of gas flowing around the intake nozzle.

Figure 2:
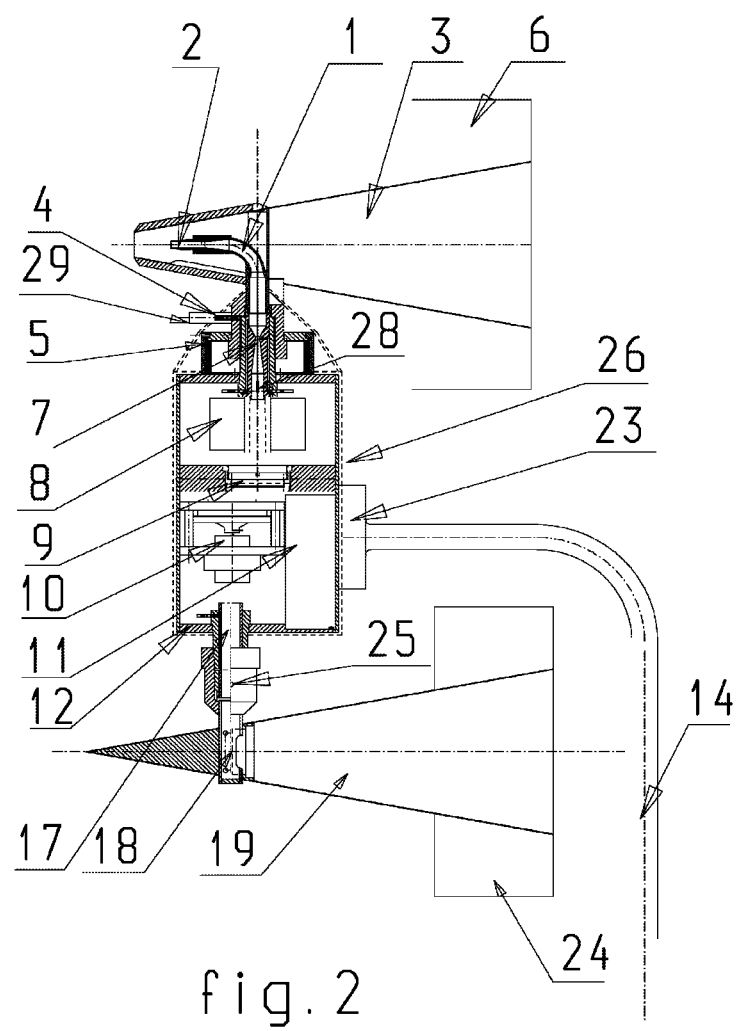
Figure 3:
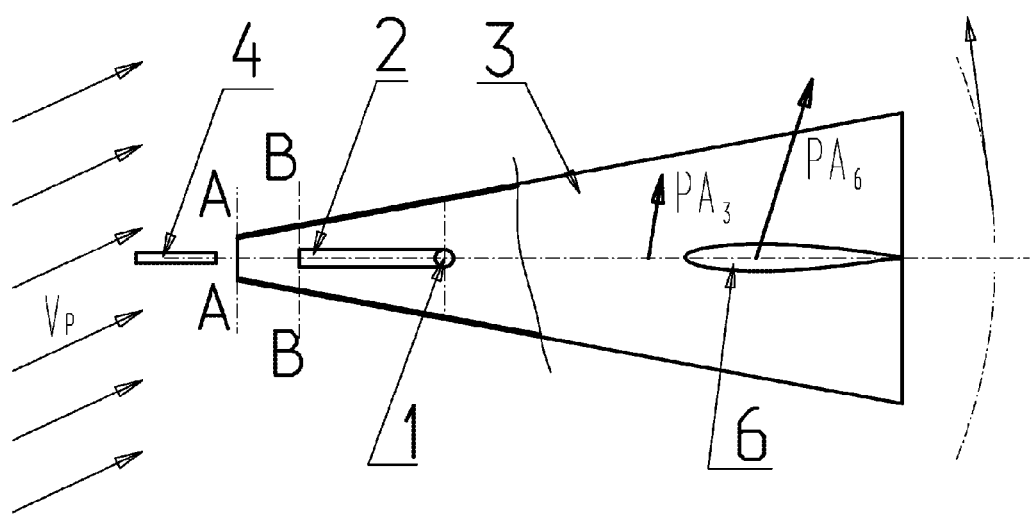
Figure 4:
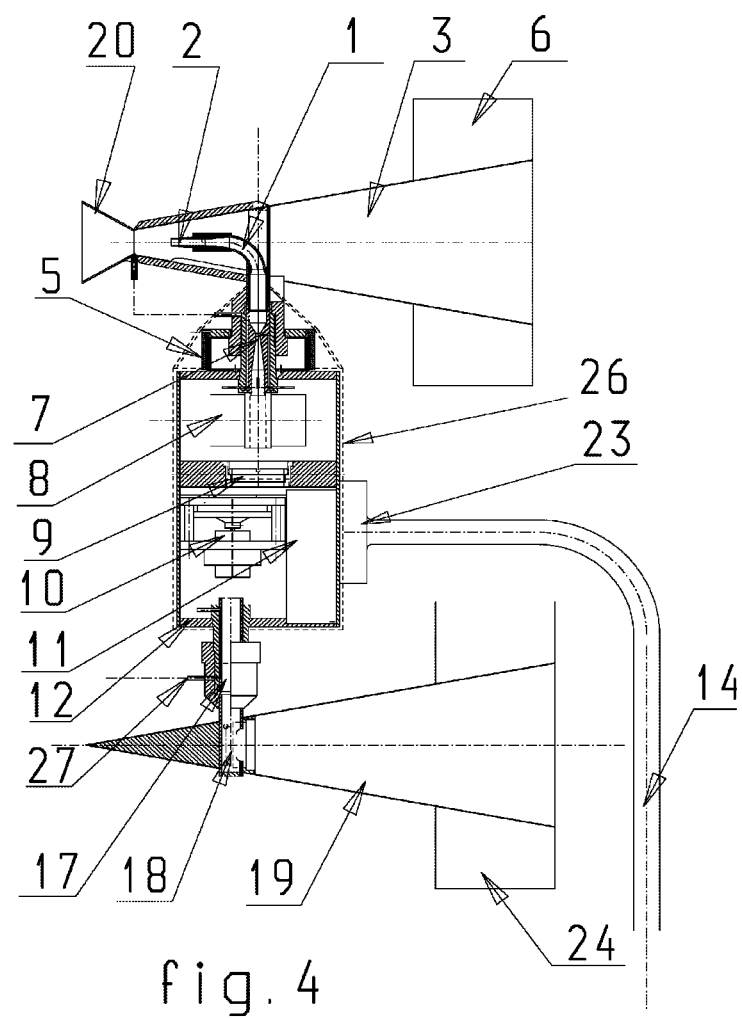
Figure 5:
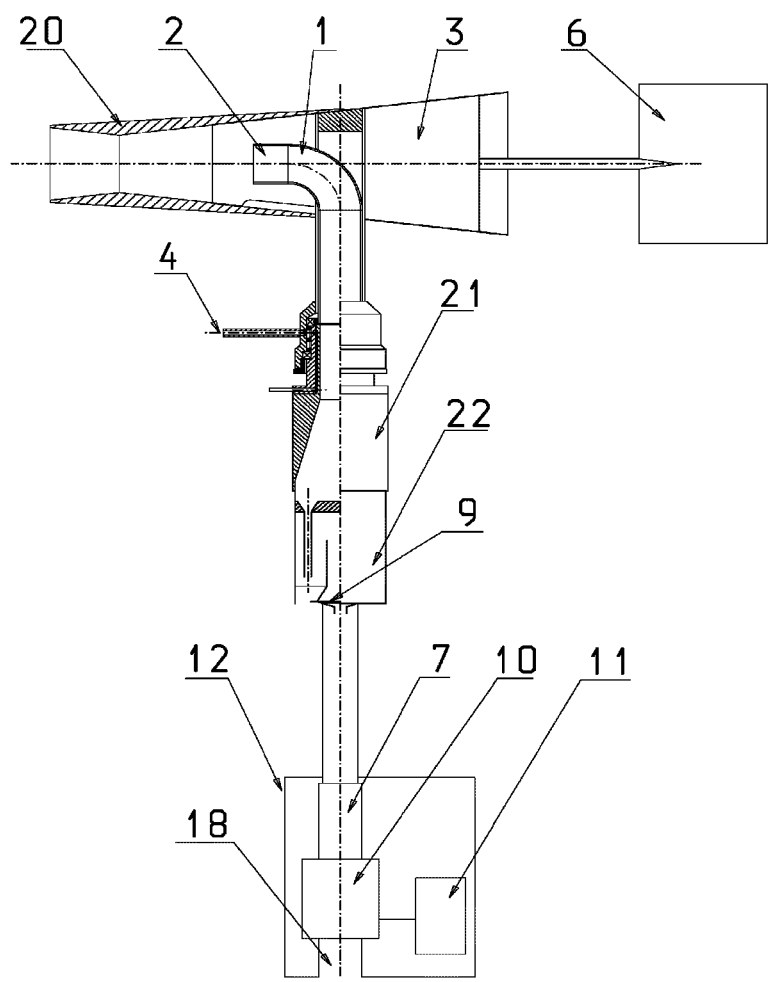

The subject of the present invention is presented using examples of construction depicted on drawings, where FIG. 1 shows a general diagram of the measuring circuit with the device for measuring dust concentration of flowing gas, FIG. 2 shows the longitudinal section of the device for measuring dust concentration according to the first example of construction, FIG. 3 shows the top view of the control unit of the device shown on FIG. 2, FIG. 4 shows the longitudinal section of the gas sample taking unit being the part of the device for measuring gas concentration in flowing gas according to the second example of construction, and FIG. 5 shows the device for measuring dust concentration in flowing gas, wherein the unit for taking the gas sample is built in the form of an attachment put on the dust sampler, that is currently in use.

The device shown on FIGS. 1 and 2 includes the feeding pipe 1 equipped with the intake nozzle 2; the said feeding pipe 1 is rigidly joined with the control unit having the form of an open diffuser 3, also joined with the meter for measuring the velocity of flowing air, the said meter consisting of a Pitot tube assembly 4 and openings 25, and also joined with a wind rose meter 5 for measuring the direction of wind. The intake nozzle 2 is coaxially located inside the diffuser 3, and the inlet of the intake nozzle 2 is directed to this end of diffuser 3 which has a smaller diameter. The diffuser 3 is equipped with two vertical stabilisers 6. The end of the feeding pipe 1 opposite to the intake nozzle 2 is connected in a rotary manner with the unit for measuring inner flow parameters, the said unit is built in the form of a Venturi tube into which the optical fibre 28 is inserted that delivers laser light for evaporating water drops. The Venturi tube 7 connects rigidly with the optical/electronic particle sensor 8. Below the particle sensor 8 there is a filter 9 installed in the socket located near the inlet of the centrifugal suction pump 10. Next to the suction pump 10 there is the chamber 11 containing electronic preamplifiers for measuring sensors. The Venturi tube 7, particle sensor 8, filter 9, suction pump 10, and chamber 11 are all located inside the immovable body 12 that is joined with the rigid expansion arm 14 by using a hermetic electrical connector with the lock 23. A multi-conductor cable that connects all measuring sensors with electronic measuring block (EMB) 15, and then with the computer 16, goes through the extension arm 14 and the base 13. The exhaust pipe 17 equipped with the exhaust nozzle 18 is joined in a rotary manner with the bottom of the body 12, and is also hermetically joined with the conical fairing 19, whereas the exhaust nozzle 18 is located inside the said conical fairing 19, and the outlet of the exhaust nozzle 18 is directed towards the base of the conical fairing 19. The entire surface of the body 12 is covered with insulating foam 26, and inside the said body a thermoregulator is installed.

An example of construction of the present invention shown on FIG. 4 differs from the one shown on FIG. 2—the diffuser 3 from its end with a smaller diameter has a different structure, since in this construction the diffuser 3 from the side of the smaller diameter end is shaped in the form of a Venturi tube 20, which is employed as one of pressure measurement points for the flowing gas velocity meter. The Pitot tube 27 plays a role of the second pressure measurement point. The meter of flowing gas velocity in such an arrangement is more accurate than the combination of the Pitot tube 4 and openings 25 shown on FIG. 2 and allows for a more isokinetic measurement by more accurate control of the suction pump 10.

In the example of construction shown on FIG. 5, the end of the feeding pipe 1 opposite to the intake nozzle 2 is joined in a rotary manner with the intermediate chamber 21 which is hermetically put on the head 22 of the dust sampler, for example the dust sampler described in the European standard N° EN 12341 or another dust sampler, particularly a dust sampler employing measurement methods like TEOM (Tapered Element Oscillating Microbalance), FDMS (Filter Dynamic Measurement System), ELPI (Electrical Low Pressure Impactor), and ADMSS (Automatic Dust Monitor and Sequential Sampler). The dimensions of intermediate chamber 21 should be adjusted to the dimensions of the dust sampler head 22 to allow these units to be joined tightly.

In the device depicted on FIG. 5 the flow should be controlled in a way making it possible to meet the isokinetic condition in the intake nozzle 2, as determined by comparing the results of flowing gas velocity measurements taken by using the Pitot tube 4 and the internal flowmeter, for example the Venturi tube.

The device shown on FIG. 1-4 operates as follows: the diffusers 3 and fairing 19, due to their geometrical shape and the presence of stabilizers 6 and 24, always position themselves against the wind. If the axis of diffuser 3 is not parallel to the direction of the wind, then under the influence of wind velocity $V_p$ the aerodynamic forces $PA_3$ and $PA_6$ (see FIG. 3) appear and act on the diffuser 3 and stabilizer 6, respectively; the same situation occurs for the lower fairing 19. These forces position the diffuser 3 with the intake nozzle 2 against the wind. Similarly, the Pitot tube 4 always positions itself against the wind, since it is rigidly joined with the diffuser 3 through the feeding pipe 1. Differential pressure between the inlet of the intake nozzle 2 and outlet of the exhaust nozzle 18 generates the air flow which depends on the wind speed. If air velocity in the inlet of the intake nozzle 2 is smaller than velocity of air flowing around the said nozzle 2, an electronically controlled suction pump 10 starts. The value of air velocity in the inlet of the intake nozzle 2 is calculated based on the measurement of flow through the Venturi tube 7. Wind speed is measured by using the combination of the Pitot tube 4 and openings 25, or by using the Prandtl tube, or by using the combination of the Pitot tube 27 and Venturi tube 20.

Downstream the Venturi tube 7 the air flows into the optical/electronic particle sensor 8. This sensor consists of a source of radiation, measuring space, and a photovoltaic cell connected to the electronic measuring circuit. The measuring space is formed by optical systems. When a particle of dust appears in this space, then, due to optical phenomena, the radiation incident on the photovoltaic cell changes, which causes generation of an electrical pulse in electronic circuit. On this basis, the size and quantity of dust particles and their variation in time can be determined. Values of mass and volume percentages of any size class of suspended dust are visualized on the screen of computer 16. The particle sensor 8 may be used for online measurements and sizes of dust particles and further the content of any size class of suspended dust may be determined. To determine the absolute mass of any size class it is necessary to weigh all dust captured by the device where the dust was previously measured optically, then separated in the filter 9. Preferably, the particle sensor can be equipped with additional optics that forms a NIRS system. Clean air flows through a suction pump 10, then through an exhaust tube 17 with an exhaust nozzle 18, and finally gets out the device through a conical fairing 19. The conical fairing 19, thanks to its geometrical shape, always positions its open base with the wind.

In the device illustrated on FIG. 5, the gas sample taking module operates in a similar way as in the device depicted on FIG. 1-4. The mass of dust captured in the device is determined by weighing the dust separated in the filter 9. Clean air passes through a suction pump 10 and then gets out of the device through an exhaust nozzle 18.

EXAMPLE

The measurement of dust concentration in atmospheric air was carried out. In the device used for this measurement and shown on FIG. 1-3, the diameter D of a smaller opening of the diffuser 3 (section A-A, FIG. 3) was 25 mm; the diameter $D_{B-B}$ of the diffuser 3 at the inlet of the intake nozzle 2 (section B-B) was 37 mm; the diameter $d_z$ of the intake nozzle was 7 mm; and minimum diameter $d_v$ of the Venturi tub was 4 mm. Aerodynamic forces $PA_3$ and $PA_6$ (see FIG. 3) have positioned both the diffuser 3 with intake nozzle 2 and the Pitot tube 4 strictly against the wind. Then the readout of wind speed measured by the Pitot tube 4 was made, and the result was $V_p=8.35$ m/s. The intake nozzle 2 is positioned inside the divergent diffuser 3, so the wind speed in the B-B section was:

$$V_{B-B}=V_p \times D^2/D_{B-B}^2=8.35 \times 25^2/37^2=3.81 \text{ m/s}.$$

To meet the isokinetic condition, the velocity of the measuring stream in the inlet of the intake nozzle should be the same, whereas the corresponding velocity in the minimal cross-section of the Venturi tube 7 should amount to:

$$V_v=V_{B-B} \times d_z^2/d_v^2=3.81 \times 7^2/4^2=11.67 \text{ m/s}.$$

The actual initial value of the measuring stream in the Venturi tube 7 was 8.2 m/s. Results of measurements taken by measuring sensors were transmitted electrically to the electronic measuring module 15, which turned on the suction pump 10 and then the rotational speed of the said pump has been automatically stabilised on the level ensuring that the velocity of the measuring stream in the Venturi tube 7 amounts to 11.67 m/s.

The measurement was taken during the period of 17 minutes and 31 seconds. The volume of air sucked in the device was 154 dm³. The total number of dust particles was measured with the result of 529 particles with total mass of 0.924 µg (the latter was determined by measuring the increment in the mass of the filtering baffle in filter 9). These figures led to an overall number of particles in 1 m³ of air equal to 3435 and an overall mass of these particles equal to 6 µg. Moreover, air parameters were measured and it was found that the temperature was 24° C. and humidity was 69.31% at the assumed density of dust particles equal to 2.54 g/cm³.

The invention claimed is:

1. A method of measuring dust in a flowing gas, comprising:
    a) measuring a first velocity of the flowing gas through an intake nozzle,
    b) measuring a second velocity of the flowing gas along the direction of gas flow,
    c) in the gas flowing through the intake nozzle, at least one of measuring dust particle size, separating out dust, or a combination thereof,
    wherein in (c) the intake nozzle is continuously positioned aerodynamically along the direction of gas flow,
    wherein two independently movable conically shaped members, a diffuser and a fairing, are positioned along the direction of gas flow, wherein the two members include vertical stabilisers, wherein the diffuser includes the intake nozzle therein and the fairing has a form of a deflector and includes an exhaust nozzle therein,
    d) comparing the first velocity of the flowing gas through the intake nozzle with the second velocity of the flowing gas around the intake nozzle, and
    e) reducing the eventual differences between the first and second velocities by changing a velocity of the gas flowing through the intake nozzle between the diffuser and the fairing with a suction pump.

2. A method according to claim 1, wherein the velocity of the flowing gas in an inlet of the intake nozzle is determined based on geometric inner parameters of the diffuser and a flow of the flowing gas through a reducing pipe.

3. A method according to claim 1, further comprising evaporating water drops present in the flowing gas that are sucked into the nozzle using laser light delivered to the flowing gas through an optical fiber located at a wider end of the reducing pipe and directed upwards along an axis of the reducing pipe towards a narrower end of the reducing pipe.

4. A device for measuring dust in a flowing gas comprising:
    a feeding pipe with an intake nozzle having an inlet,
    a particle sensor and optionally a filter,
    an immovable body that contains a unit that is operative to measure flow parameters including temperature and humidity, and
    a first velocity meter that is operative to measure velocity of the flowing gas through the intake nozzle, wherein the feeding pipe is hermetically connected to the first velocity meter,
    a second velocity meter that is operative to measure velocity of the flowing gas around the intake nozzle;
    a suction pump with a control circuit, wherein the control circuit is operative to control the suction pump responsive at least in part to the first and second velocity meters,
    an exhaust pipe including an exhaust nozzle,
    a controlling element having the form of an open diffuser,
    a conical fairing,
    wherein the intake nozzle is positioned inside the diffuser, wherein the inlet of the intake nozzle is directed towards that end of the diffuser which has a smaller diameter, wherein an end of the feeding pipe located opposite to the intake nozzle is connected in a rotary manner to the unit that is operative to measure flow parameters, wherein the subsequently connected are the following: the particle sensor, the suction pump and rotationally the exhaust pipe with the exhaust nozzle joined with the conical fairing, wherein the exhaust nozzle is located inside the conical fairing and an outlet of the exhaust nozzle is directed towards a wider end of the conical fairing.

5. The device according to claim 4, wherein the diffuser and the conical fairing include at least one vertical stabiliser located near the wider ends of each one of the diffuser and the conical fairing, and wherein the diffuser at the narrower end is shaped in the form of a Venturi tube used as a first part of the first velocity meter that measures the velocity of flowing gas through the intake nozzle, wherein a second part of the first velocity meter has the form of a Pitot tube located above the conical fairing, and wherein the intake nozzle and the diffuser are arranged coaxially.

6. The device according to claim 4, wherein the immovable body is covered with insulating foam and a temperature regulator is located inside the immovable body.

7. The device according to claim 4, wherein the feeding pipe is joined with the second velocity meter, wherein the second velocity meter is an electric or magnetic device.

8. The device according to claim 4, wherein the first velocity meter that measures the velocity of flowing gas through the intake nozzle includes, as a first part, a Pitot tube located under the diffuser and, as a second part, openings located above the conical fairing perpendicularly to the axis of the conical fairing, and wherein the first velocity meter that measures the velocity of flowing gas through the intake nozzle is a combination of a further Pitot tube and a Venturi tube, and wherein the further Pitot tube has an additional shield in the form of a pipe with a greater diameter and equipped with a further filter.

9. The device according to claim 4 or 8, wherein the second velocity meter includes a magnetic sensor that is situated beyond the axis of rotation of a portion of the second velocity meter.

10. The device according to claim 4, wherein the unit for measuring flow parameters is built in the form of a Venturi tube, and the unit that is operative to measure flow parameters is equipped with humidity and temperature sensors and an optical fibre that is configured to evaporate water particles.

11. The device according to claim 4, wherein the particle sensor is built in the form of an optical/electronic particle sensor that is optionally equipped with a Near Infrared Spectroscope (NIRS).

12. The device according to claim 4, further comprising the filter located between the particle sensor and the suction pump.

13. The device according to claim 4, or 10, or 11, or 12, wherein the unit that is operative to measure flow parameters, the particle sensor, the suction pump and the filter are all located inside the immovable body fixed to a base, optionally through a rigid extension arm.

14. The device according to claim 13, wherein a hermetic electrical connection exists between the immovable body and the extension arm and this connection is operative to be blocked using a lock.

* * * * *